(12) United States Patent
Yamaki et al.

(10) Patent No.: US 8,491,573 B2
(45) Date of Patent: Jul. 23, 2013

(54) COMMUNICATION CONVERTER, ITS SYSTEM AND ITS METHOD

(75) Inventors: Masahide Yamaki, Tokyo (JP); Shusuke Tsuchiya, Tokyo (JP); Kiyoshi Sekiguchi, Tokyo (JP)

(73) Assignee: Olympus Medical Systems Corp. (JP)

( * ) Notice: Subject to any disclaimer, the term of this patent is extended or adjusted under 35 U.S.C. 154(b) by 1465 days.

(21) Appl. No.: 12/122,769

(22) Filed: May 19, 2008

(65) Prior Publication Data

US 2009/0287065 A1   Nov. 19, 2009

(51) Int. Cl.
*A61B 17/00* (2006.01)

(52) U.S. Cl.
USPC .............................................. 606/1

(58) Field of Classification Search
None
See application file for complete search history.

(56) References Cited

U.S. PATENT DOCUMENTS

| | | | | |
|---|---|---|---|---|
| 6,259,706 B1 * | 7/2001 | Shimada | ........................ | 370/466 |
| 6,268,999 B1 * | 7/2001 | Tg | ............................ | 361/679.02 |
| 6,405,254 B1 * | 6/2002 | Hadland | ....................... | 709/230 |
| 6,433,825 B1 | 8/2002 | Cama et al. | | |
| 6,434,644 B1 * | 8/2002 | Young et al. | ..................... | 710/63 |
| 6,524,240 B1 * | 2/2003 | Thede | ........................... | 600/300 |
| 6,601,115 B1 * | 7/2003 | Yonezawa et al. | ............... | 710/11 |
| 6,636,010 B1 * | 10/2003 | Malmstrom et al. | .......... | 318/644 |
| 2002/0163514 A1 * | 11/2002 | Nagai et al. | .................... | 345/204 |
| 2005/0017321 A1 * | 1/2005 | Hakkarainen et al. | ........ | 257/532 |

FOREIGN PATENT DOCUMENTS

| | | |
|---|---|---|
| JP | 07-039514 | 2/1995 |
| JP | 10-101243 | 4/1998 |
| JP | 11-299781 | 11/1999 |

OTHER PUBLICATIONS

Popovich, M. et al. On-Chip Power Noise Reduction Techniques in High Performance SoC-Based Integrated Circuits. IEEE International SOC Conference, Sep. 19-23, 2005, Proceedings, pp. 309-312.*

* cited by examiner

*Primary Examiner* — Robert A Wax
*Assistant Examiner* — Olga V Tcherkasskaya
(74) *Attorney, Agent, or Firm* — Ostrolenk Faber LLP

(57) ABSTRACT

A communication converter converts a communication system and/or a communication protocol to enable communications to be performed between medical equipment and a medical control device for controlling the medical equipment, and includes: a primary substrate on which a control unit for controlling the communication converter is arranged; n (n indicates any integer) pieces of secondary substrate electrically isolated from the primary substrate and the housing of the communication converter; and n (n indicates any integer) pieces of grounding switch unit corresponding to each of the n pieces of secondary substrate for switching the grounding state of the secondary substrate.

10 Claims, 18 Drawing Sheets

| SWITCH STATUS OF SWITCH TERMINAL | SWITCHING TYPE | GROUNDING STATE | CONTENTS | RELATIONSHIP BETWEEN NOISE AND LEAKAGE CURRENT |
|---|---|---|---|---|
| Sw_A | A | TO BE GROUNDED | INTENSIFYING SHIELDING EFFECT | NOISE : DECREASING<br>LEAKAGE CURRENT : INCREASING |
| Sw_B | B | NOT TO BE GROUNDED | REDUCING SHIELDING EFFECT | NOISE : INCREASING<br>LEAKAGE CURRENT : DECREASING |
| Sw_C | C | CONNECTED AT HIGH FREQUENCY (DC CAPACITOR) | SINCE HIGH FREQUENCY CONNECTION IS MADE, SHIELDING EFFECT CAN BE OBTAINED. SINCE ELECTRICALLY ISOLATED, NO DC CURRENCT (LEAKAGE CURRENT) PASSES. | NOISE : DECREASING (WHEN HIGH FREQUENCY ARISES)<br>LEAKAGE CURRENT (DC) : DECREASING |

FIG.11

| NAME OF MEDICAL EQUIPMENT | SWITCHING TYPE |
|---|---|
| P1 | A |
| P2 | B |
| P3 | C |
| ⋮ | ⋮ |

FIG.12

| NAME OF MEDICAL EQUIPMENT | SWITCHING TYPE | FIRST GROUNDING SWITCH UNIT | ... | n-TH GROUNDING SWITCH UNIT |
|---|---|---|---|---|
| P1 | A | Sw_B | ... | Sw_A |
| P2 | B | Sw_A | ... | Sw_B |
| P3 | C | Sw_C | ... | Sw_C |
| ⋮ | ⋮ | ⋮ | ⋮ | ⋮ |

FIG.17

COMMUNICATION CONVERTER, ITS SYSTEM AND ITS METHOD

FIELD OF THE INVENTION

The present invention relates to a communication converter for connecting a plurality of medical devices to a medical control device for controlling the medical devices.

BACKGROUND OF THE INVENTION

Recently, surgery is performed using an endoscope operation system having a plurality of medical devices. In an endoscope operation system, an organization of a living body is removed using an abdomen insufflation unit for expanding a visceral cavity and a treating device etc. for treating an affected part, and hemostasis is performed using a high frequency cautery device, and these treatments can be performed while watching images captured by an endoscope.

The endoscope operation system includes a plurality of medical devices for an endoscope operation, and a system controller for controlling the medical devices, a display operation device, etc. Thus, since the endoscope operation system is configured by a plurality of devices, it is necessary to use a common communication protocol to enable communications among the devices to be performed. However, manufacturers of medical devices usually adopt different communication methods and/or communication protocols for their own medical devices. Therefore, a communication converter is used to convert the communication methods and/or communication protocols to enable communications to be performed between them.

The communication system refers to a system of communications based on the physical or electrical configuration of communications such as infrared communications, USB (universal serial bus) communications, RS-232C communications, controller area network (CAN), or Ethernet communications, etc. A difference in communication system refers to a difference in physical or electrical standards in various communications such as a difference between wireless communication and cable communication, a difference in shape of a connector, etc. (Therefore, the difference disables a physical or electrical connection to be performed). A communication protocol refers to a normally adopted communication protocol, that is, a logical connection, as compared with the physical or electrical connection in the above-mentioned communication system.

Generally, medical equipment is covered with a metal housing. The metal housing contains a substrate for operating the medical equipment. The substrate is fixed to the metal housing by metal fittings, and the metal housing is grounded in many cases. Thus, the noise occurring from the electronic components on the substrate can be prevented from being transmitted outside the housing, thereby reducing the influence of the noise to another equipment unit. In addition, the influence of the noise from other equipment units to the medical equipment can be minimized.

SUMMARY OF THE INVENTION

A communication converter according to the present invention converts a communication system and/or a communication protocol to enable the communication to be performed between medical equipment and a medical control device for controlling the medical equipment, and includes: a primary substrate on which a control unit for controlling the communication converter is arranged; n pieces of (n indicates any integer) secondary substrate electrically isolated from the primary substrate and the housing of the communication converter; and n (n indicates any integer) pieces of grounding switch unit corresponding to each of the n pieces of the secondary substrate for switching the grounding state of the secondary substrates.

An operation system according to the present invention has medical equipment, a medical control device for controlling the medical equipment, and a communication converter for converting a communication system and/or a communication protocol to enable the communication to be performed between medical equipment and a medical control device for controlling the medical equipment. In the operation system, the communication converter includes: a primary substrate on which a control unit for controlling the communication converter is arranged; n (n indicates any integer) pieces of secondary substrate electrically isolated from the primary substrate and the housing of the communication converter; and n (n indicates any integers) pieces of grounding switch units corresponding to each of the n pieces of the secondary substrate for switching the grounding state of the secondary substrates.

In the method for adjusting the grounding state of a communication converter which converts a communication system and/or a communication protocol to enable the communication to be performed between medical equipment and a medical control device for controlling the medical equipment, the communication converter includes: a primary substrate on which a control unit for controlling the communication converter is arranged; n (n indicates any integer) pieces of secondary substrates electrically isolated from the primary substrate and the housing of the communication converter; n (n indicates any integer) pieces of grounding switch units corresponding to each of the n pieces of the secondary substrates for switching the grounding state of the secondary substrates; and a storage unit for storing the grounding information relating to the grounding of the i-th (i=1~n) secondary substrate for each unit of the medical equipment. With the configuration, when the medical equipment is connected, the control unit reads the grounding information corresponding to the medical equipment from the storage unit, and controls the grounding switch unit according to the grounding information.

BRIEF DESCRIPTION OF THE DRAWINGS

FIG. 11 shows the relationship between the electrical noise and the leakage current caused by switching of the grounding switch unit 621 according to the first embodiment of the present invention;

FIG. 12 shows an example of grounding information 1201 by equipment according to the first embodiment of the present invention;

FIG. 17 shows an example of grounding information by equipment according to the second embodiment (variation example) of the present invention.

DETAILED DESCRIPTION OF THE INVENTION

<First Embodiment>

Figure 1:
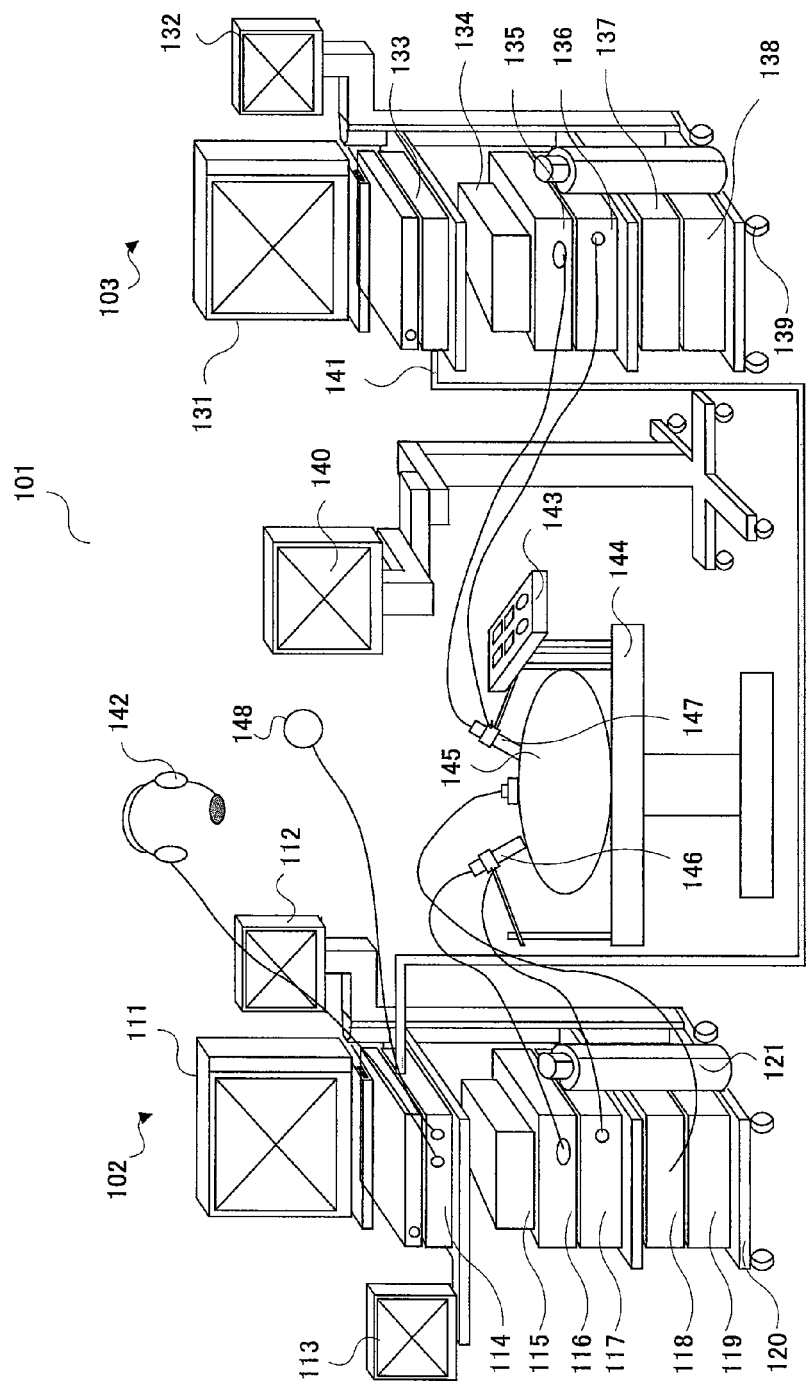
FIG. 1 shows the entire configuration of the endoscope operation system according to the first embodiment of the present invention.

FIG. 1 shows the entire configuration of the endoscope operation system according to an embodiment of the present invention. An endoscope operation system 101 is provided on both sides of a bed 144 for a patient 145 with a first endoscope operation system 102, a second endoscope operation system 103, and an operator's wireless remote controller 143.

In the endoscope operation systems 102 and 103, a plurality of endoscope related medical devices for performing observation, inspection, treating, and recording, etc. are loaded onto a first trolley 120 and a second trolley 139. A movable stand is loaded with an endoscope display panel 140.

The first trolley 120 includes an endoscope display panel 111, a central display panel 112, a central operation panel device 113, a system controller 114, a recorder 115, a video processor 116, an endoscope light source device 117, an abdomen insufflation device 118, and an electric knife device 119.

The central operation panel device 113 is arranged in a unsterilized area, and nurses etc. centrally perform operations of medical devices. A mouse, a touch panel, etc. not shown in the attached drawings can be provided for the device. Using the central operation panel device 113, medical devices can be centrally managed, controlled, and operated.

Each medical device is connected to the system controller 114 through a communication cable such as a serial interface cable etc., not shown in the attached drawings, to perform bi-directional communications with a system controller.

Additionally, a head set type mike 142 can be connected to the system controller 114. The system controller 114 may recognize the voice input from the head set type mike 142, and can control each device by the voice of an operator. Furthermore, a speaker 148 can be connected to the system controller 114.

The endoscope light source device 117 is connected to a first endoscope 146 through a light guide cable for transmitting illumination light. When the illumination light of the endoscope light source device 117 is supplied to the light guide of the first endoscope 146, it illuminates the affected part etc. in the belly of the patient 145 into which the insertion part of the first endoscope 146 is needled.

The optical image data captured by the camera head of the first endoscope 146 is transmitted to the video processor 116 through the camera cable. The optical image data is signal-processed in the signal processing circuit in the video processor 116, thereby generating a video signal.

The abdomen insufflation device 118 provides $CO_2$ gas from a gas bomb 121 inside the belly of the patient 145.

The second trolley 139 is loaded with an endoscope display panel 131, a central display panel 132, a relay unit 133, a recorder 134, a video processor 135, an endoscope light source device 136, and other medical devices 137 and 138 (for example, an ultrasonic processing device, a lithotripsy device, a pump, a shaver, etc.). Each device is connected to the relay unit 133 via a cable not shown in the attached drawings for bi-directional communications. The system controller 114 is connected to the relay unit 133 by a relay cable 141.

The endoscope light source device 136 is connected to a second endoscope 147 through a light guide cable for transmitting illumination light. The illumination light of the endoscope light source device 136 is supplied to the light guide of the second endoscope 147. Then, it illuminates the affected part etc. in the belly of the patient 145 into which the insertion part of the second endoscope 147 is needled.

The optical image data captured by the camera head of the second endoscope 147 is transmitted to the video processor 135 through a camera cable. The optical image data is signal-processed by the signal processing circuit in the video processor 135, thereby generating a video signal. Then the video signal is output to the endoscope display panel 131, and an endoscope image of an affected part etc. is displayed on the endoscope display panel 131.

The system controller 114 can also be controlled by the operator's wireless remote controller 143 with which an operator performs the operation of the device from a sterilized area. In addition, the first trolley 120 and the second trolley 139 can be loaded with other devices (for example, a printer, an ultrasonic observation device, etc.).

Figure 2:
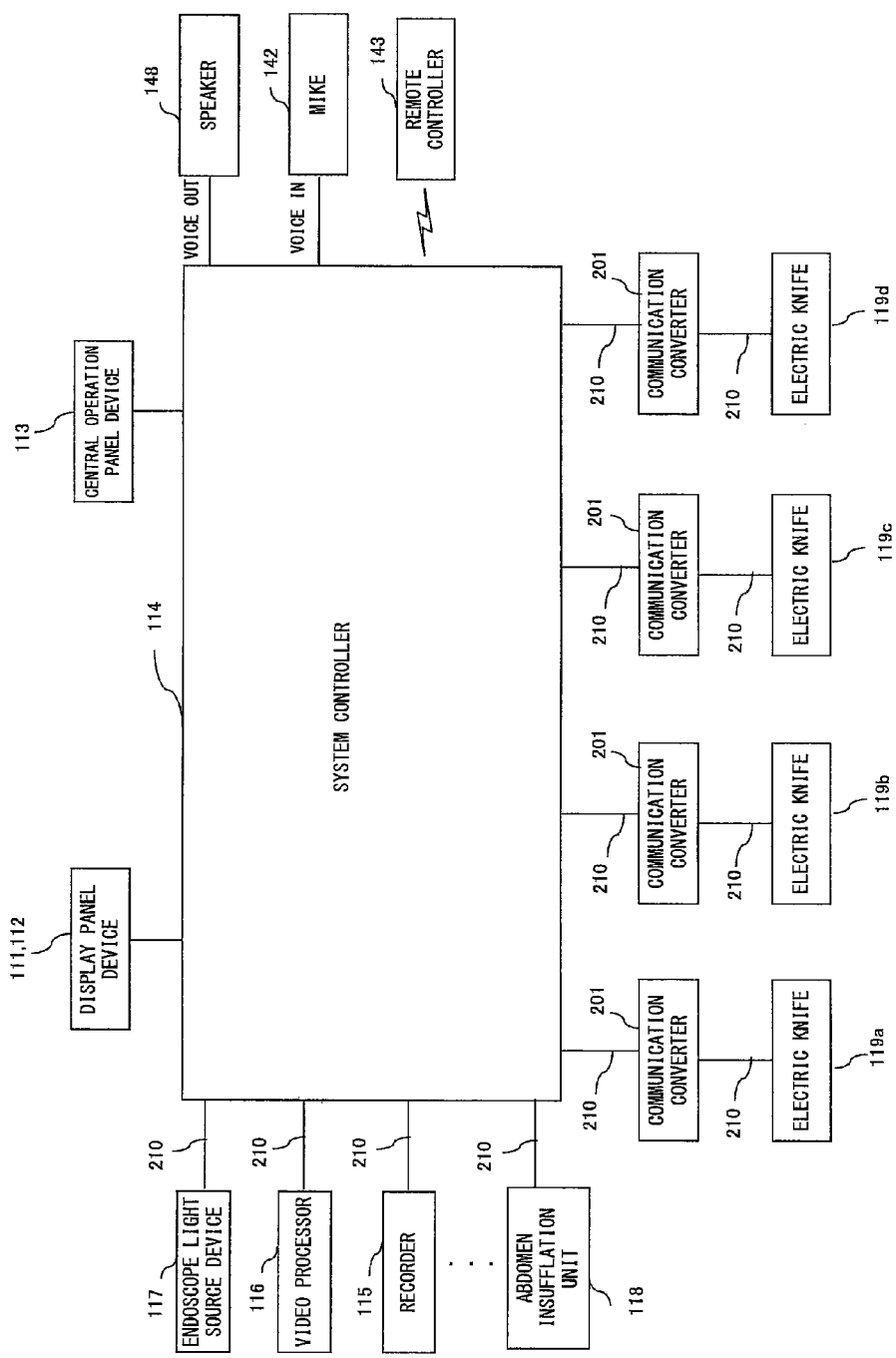
FIG. 2 is a system wiring diagram between a system controller 114 and a medical device configuring an endoscope operation system 1 according to the first embodiment of the present invention.

FIG. 2 is a system wiring diagram between the system controller 114 and the medical device configuring the endoscope operation system 1. As shown in FIG. 2, the display panel devices 111 and 112, and the central operation panel device 113 are connected to the system controller 114. Also, the head set type mike 142 for inputting voice and the speaker 148 for outputting voice are connected to the system controller 114. Further connected to the system controller 114 are medical devices such as the endoscope light source device 117, the video processor 116, the recorder 115, . . . , the abdomen insufflation device 118, electric knife devices 119a 119b, 119c, 119d, etc. through the communication passage 210 by cable or by wireless.

When the communication system or the communication protocol of a medical device is different from that of the system controller 114, the medical device and the system controller 114 are connected through the communication converter 201. In FIG. 2, the electric knife devices 119a 119b, 119c, and 119d are connected to the system controller 114 through the communication converter 201.

Figure 3:
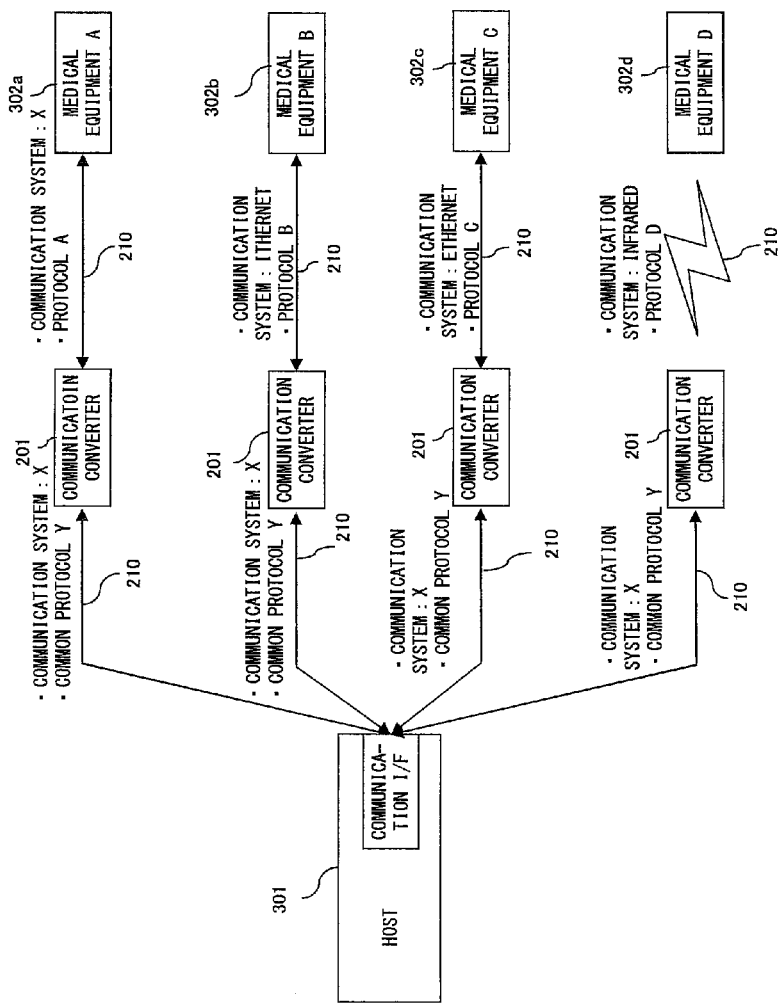
FIG. 3 is an explanatory view of the communication converter for converting the communication method and/or the communication protocol between the host computer and the medical equipment according to the first embodiment of the present invention.

FIG. 3 is an explanatory view of the communication converter for converting the communication method and/or the communication protocol between the host computer and the medical device according to the present embodiment. The connection between the host computer and a medical device adopting a communication method or a communication protocol different from the communication method or the communication protocol adopted by the host computer is described below with reference to FIG. 3. A host computer (hereinafter referred to as a host) 301 corresponds to the system controller 114. FIG. 3 shows an example of connecting between the host computer 301 and medical devices 302 (302a, 302b, 302c, 302d) using the communication converter 201 corresponding to the communication system and the communication protocol of each medical device 302.

The communication converter 201 connects the host computer 301 to the medical device 302 to convert the communication system and/or the communication protocol and enable the communications between the host computer 301 and the medical device 302 to be established.

The communication converter 201 is connected to the host computer 301 using a predetermined communication system and a predetermined communication protocol made common on the host computer 301 side. The communication converter 201 is connected to the medical device 302 using a predetermined communication system and a predetermined communication protocol corresponding to the communication interface (I/F) of each of the medical devices 302a, 302b, and 302c, and 302d.

In FIG. 3, the communication I/F of the host computer 301 can be connected and can establish communications using a communication system X (for example, RS-232C) and a predetermined communication protocol (hereinafter referred to as a common protocol) Y.

The communication I/F of the medical device A (302a) is performed by, for example, the communication system: X (for example, RS-232C) and using the communication protocol A. In this case, different communication protocols are used between the host computer 301 and the medical device A (302a). Therefore, the host computer 301 is connected to the medical device A (302a) through the communication converter 201 for mutually converting communication protocols.

The communication I/F of the medical device B (302b) is, for example, performed by, for example, Ethernet as a communication system, and the communication protocol B. In this case, the communication systems and the communication protocols are different between the host computer 301 and the medical device B (302b). Therefore, the host computer 301 is connected to the medical device B (302b) through the communication converter 201 for mutually converting the communication system and the communication protocol.

The communication I/F of the medical device C (302c) is, for example, performed by, for example, Ethernet as a communication system, and the communication protocol C. In this case, the communication systems and the communication protocols are different between the host computer 301 and the medical device C (302c). Therefore, the host computer 301 is connected to the medical device C (302c) through the communication converter 201 for mutually converting the communication system and the communication protocol.

In the communication I/F of the medical equipment C (302c), for example, the infrared communication as a communication system and the communication protocol C are used. In this case, the host 301 and the medical equipment D (302d) are different from each other in the communication system and the communication protocol. Therefore, the host 301 is connected to the medical equipment D (302d) through the communication converter 201 for mutually converting the communication system and the communication protocol between them.

Thus, the communication converter 201 can convert the communication system and/or the communication protocol between the host computer 301 and the medical device 302. To realize this, the communication converter 201 is provided with the communication I/Fs corresponding to the communication I/Fs of the respective medical devices (302a, 302b, 302c, 302d) and the communication programs relating to the communication protocols corresponding to the communication protocols of the respective medical devices (302a, 302b, 302c, 302d).

Figure 4:
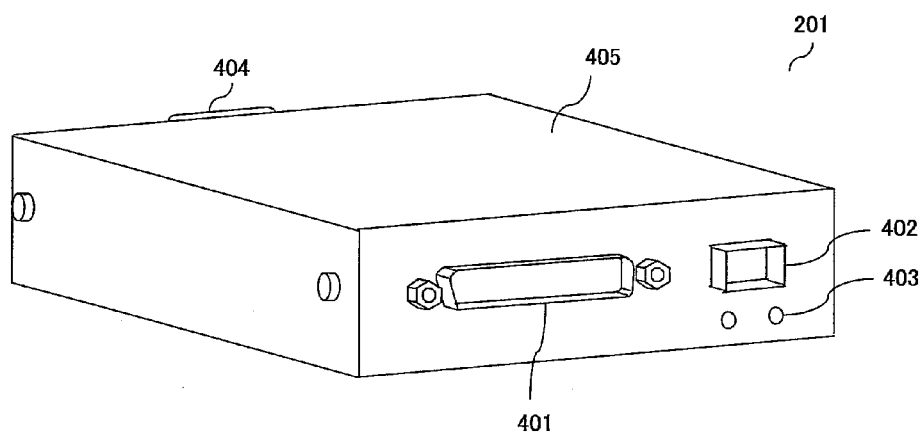
FIG. 4 shows an example of a perspective view of the housing of a communication converter 201 according to the first embodiment of the present invention.

FIG. 4 shows an example of a perspective view of the housing of the communication converter 201 according to the present embodiment. The communication converter 201 is covered with a metal housing 405. The communication I/Fs corresponding to various communication systems and communication protocols (for example, the infrared communication I/F, the Ethernet communication I/F, the serial communication I/F, etc.) are provide on the external surface of the metal housing 405 of the communication converter 201 in order to enable to connect with the medical devices using various communication systems and communication protocols.

In FIG. 4, as an example, a serial I/F (401), a CAN I/F (402), and an infrared I/F (403) are provided on the front side. Provided on the back of the housing 400 is a communication I/F 404 corresponding to the communication I/F of the host computer 301 (that is, the system controller 114). The communication I/Fs provided for the communication converter 201 are not limited to these, but can be any interface of well known standards.

Figure 5:
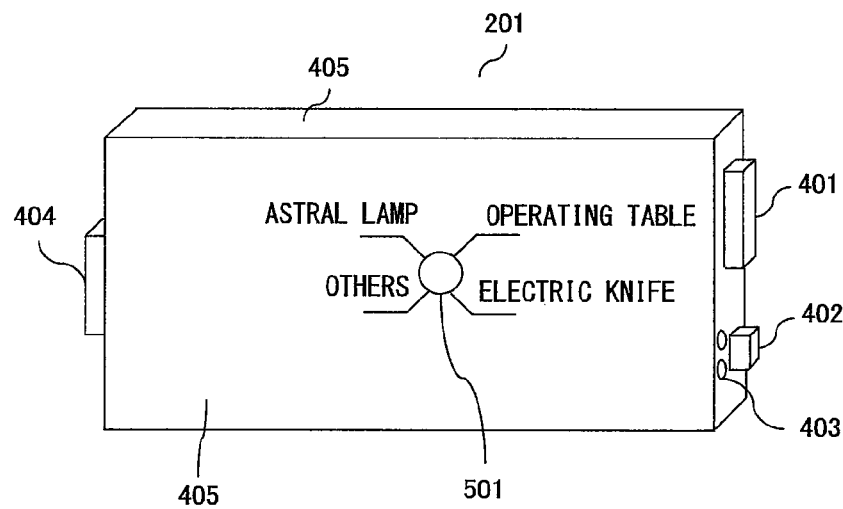
FIG. 5 shows an example of the bottom view of a housing 405 of the communication converter 201 according to the first embodiment of the present invention.

FIG. 5 is an example of a bottom view of the housing 400 of the communication converter 201 according to the present embodiment. On the bottom of the communication converter 201, a selection switch 501 for selecting a medical device to be connected is provided. In FIG. 5, a rotary switch is provided as the selection switch 501. Using the selection switch 501, for example, an "operating table", an "electric knife", an "astral lamp", and "others" categories indicating other medical devices to be connected can be selected.

The communication converter 201 downloads a communication program corresponding to the communication protocol of the medical device of the selected category. For example, when the "electric knife" is selected using the selection switch 501, the communication converter 201 can download the communication program relating to the communication protocol of the equipment "electric knife" from the host computer 301 in advance.

Figure 6:
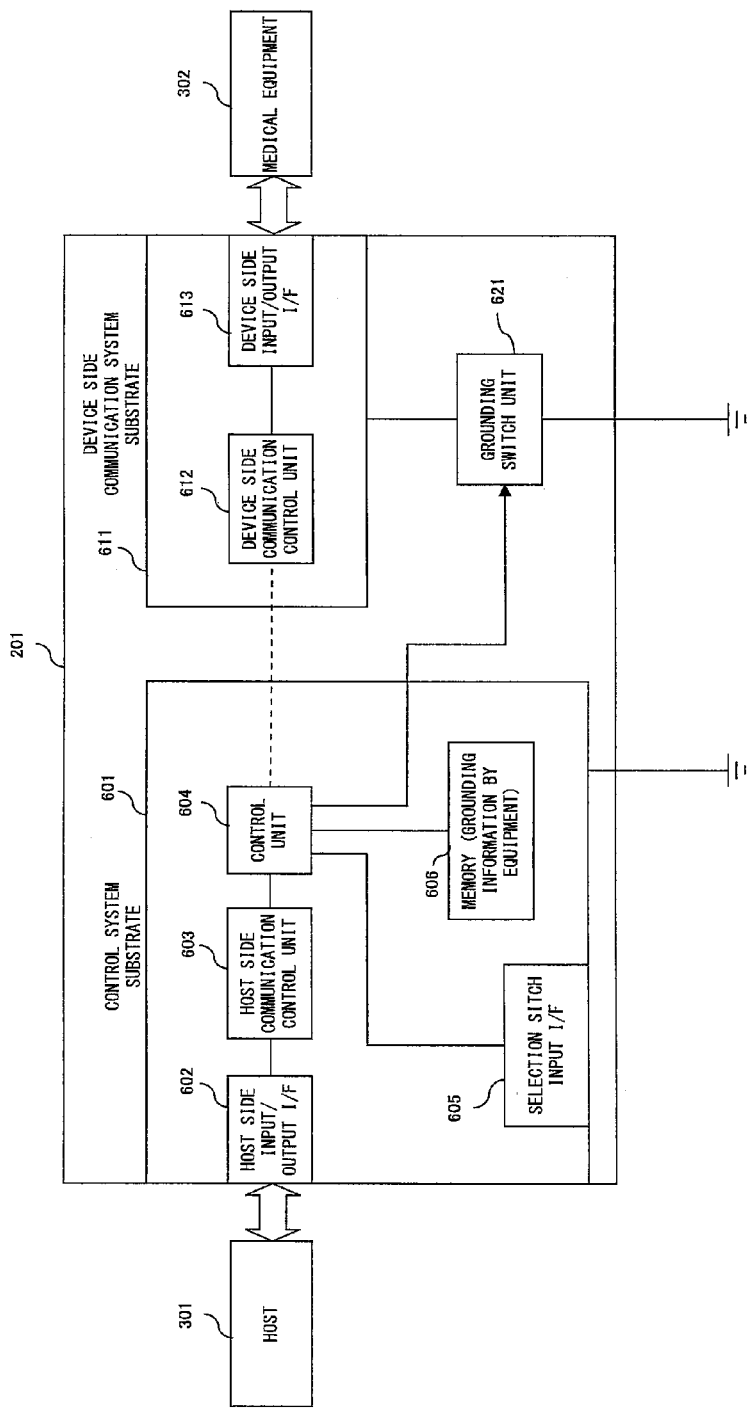
FIG. 6 shows the outline of the configuration inside the communication converter 201 according to the first embodiment of the present invention.

FIG. 6 shows the outline of the internal configuration of the communication converter 201 according to the present embodiment. A control system substrate 601, a device side communication system substrate 611, and a grounding switch unit 621 are provided in the communication converter 201. Electronic components for communications with the host 301, electronic components for controlling the main function of the communication converter 201, etc. are arranged on the control system substrate 601. Electronic components of a communication system for communications with the medical equipment 302 are arranged on the control system substrate 601. Electronic components of a communication system for communications with the medical equipment 302 are arranged on the device side communication system substrate 611.

The control system substrate 601 is provided with a host side input/output I/F 602, a host side communication control unit 603, a control unit 604, a selection switch input I/F 605, and a memory 606. The control system substrate 601 is electrically connected to the housing 405, and grounded through the housing 405.

The host side input/output I/F 602 is a communication I/F corresponding to the communication I/F of the host 301 (system controller 114), outputs data to the host 301, and receives data provided from the host 301. The host side input/output unit 602 corresponds to a communication I/F 404 shown in FIGS. 4 and 5. The host side communication control unit 603 controls the communications with the host 301.

The memory 606 stores a program relating to an embodiment of the present invention, a communication protocol downloaded from the host 301, and other programs. The memory 606 also holds the grounding information by equipment described later. The memory 606 is, for example, ROM, RAM, a hard disk drive, flash memory, etc. The memory 606 is contained in the communication converter 201, but is not limited to this application. That is, it can be externally provided (for example, a portable storage medium such as USB memory, an SD memory card, etc.).

The control unit 604 is a central processing unit for controlling the operation of each component configuring the communication converter 201, reading a program etc. stored in the memory 606, and executing the program.

The selection switch I/F 605 is an interface for the selection switch 501. The contents set by the selection switch 501 are transmitted to the control unit 604 through the selection switch I/F 605. On the basis of the set contents, the control unit 604 can download the connection program of the category of the medical equipment corresponding to the set contents.

The connection program is described below. To be connected to each medical equipment unit and communicate with the unit, a communication program corresponding to the communication protocol used by the medical equipment is required. A communication program is normally configured by a connection module, a communication sequence module, a status management module, and an error management module. The connection module determines whether or not a connection has been established with the equipment of a communication partner. After the connection is established, the communication sequence module communicates with the equipment of the communication partner on the basis of the communication protocol. The status module holds the status of a medical equipment unit defined in advance, compares the held status with the status transmitted from the equipment of the communication partner, and determines whether or not the transmitted status is correct. The error management module manages, for example, a timeout error etc. The communication converter 201 downloads a connection module (connection program) of the communication program of the category of the medical equipment set by the selection switch I/F 605. When the connected medical equipment is determined, the communication converter 201 can download the entire communication program corresponding to the connection program of the determined medical equipment or the remaining communication programs.

The device side communication system substrate 611 is electrically isolated from the metal housing 405 and the control system substrate 601 unless it is grounded by the grounding switch unit 621 described later. The device side communication system substrate 611 has a device side communication control unit 612 and a device side input/output I/F 613. The device side input/output I/F 613 is a communication I/F corresponding to the communication I/F on the device side of the medical equipment 302 etc. The I/F 613 outputs data to the 302, and receives data provided from the medical equipment 302. The device side input/output I/F 613 corresponds to the serial I/F 401, the CAN I/F 402, or the infrared I/F 403 shown in FIGS. 4 and 5. The device side communication control unit 612 controls the communications with the medical equipment 302. The device side communication control unit 612 receives an instruction from the control unit 604 through an insulating element of a photocoupler etc. and communicates data with the control unit 604.

The grounding switch unit 621 switches the grounding state of the device side communication system substrate 611 at an instruction of the control unit 604. The grounding switch unit 621 can be an analog switch, or a relay switch, etc. The grounding switch unit 621 is described later.

Figure 7:
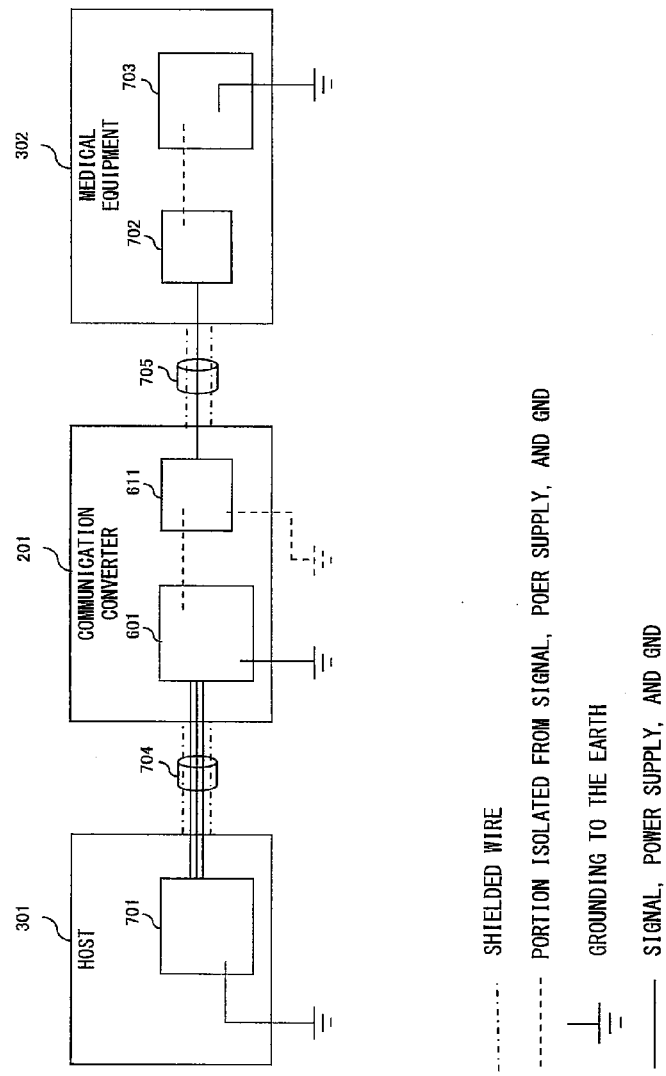
FIG. 7 shows the concept of the electric connection among a host computer 301, the communication converter 201, and medical equipment 302 according to the first embodiment of the present invention.

FIG. 7 shows the concept of the electric connection among the host 301, the communication converter 201, and the medical equipment 302 according to the present embodiment. In FIG. 7, the grounding switch unit 621 grounds the device side communication system substrate 611.

The host 301 is covered with a metal housing. The housing stores a substrate 701. The substrate 701 includes an arrangement of various circuits configuring the host 301 for communicating with a plurality of medical equipment units, processing images. The substrate 701 is grounded through the housing.

The medical equipment 302 is covered with a metal housing. The housing stores substrates 702 and 703. The substrate 702 includes an arrangement of a communication system circuit for communicating with the communication converter 201 and for remote controlling by the host 301 through the communication converter 201. The substrate 703 includes an arrangement of a control system circuit for controlling the main function such as outputting from medical equipment etc. The substrate 703 is grounded through the housing. In FIG. 7, the substrate 702 is isolated from the housing and the substrate 703 and a signal, power supply, and GND. However, the present invention is not limited to this configuration. For example, the substrates 702 and 703 can be unitary.

The host 301 and the communication converter 201 are connected through a communication cable 704 for a common protocol. The communication converter 201 and the medical equipment 302 are connected via a prescribed communication cable 705. Each of the communication cables 704 and 705 is covered with a shielded wire.

Figure 8:
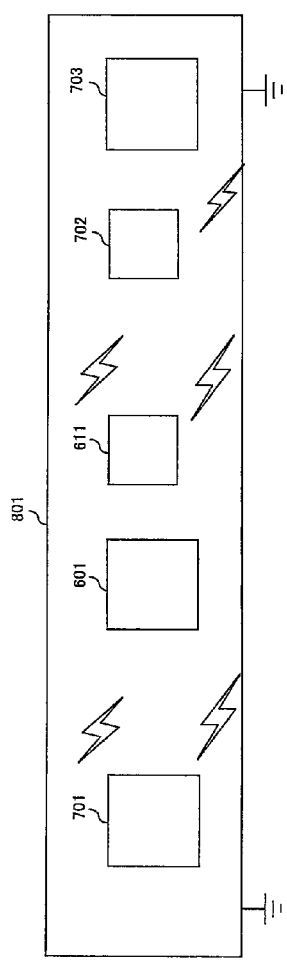
FIG. 8 shows the concept of the shield relating to the electric connection among the host computer 301, the communication converter 201, and the medical equipment 302 according to an embodiment of the present invention.

FIG. 8 shows the concept of the shielding relating to the electric connection among the host 301, the communication converter 201, and the medical equipment 302. FIG. 8 shows an image of the shielding effect based on the electric connection described above with reference to FIG. 7. As described above with reference to FIG. 7, each substrate is covered with a metal housing and grounded. The communication cables 704 and 705 are covered with a shielded wire, and grounded through the housing of each device. Thus, since the housing, the substrate, and the shielded wire are of the same potential, they are entirely shielded as shown by reference numeral 801. The shielding effect enables electronic components on the substrate in each equipment unit to be quickly processed, and the influence of noise generated by the passage of a large amount of currents on the substrate to be reduced.

However, when the shielding effect is intensified, some medical equipment units have a large influence of a leakage current, which is described below with reference to FIG. 9.

Figure 9:
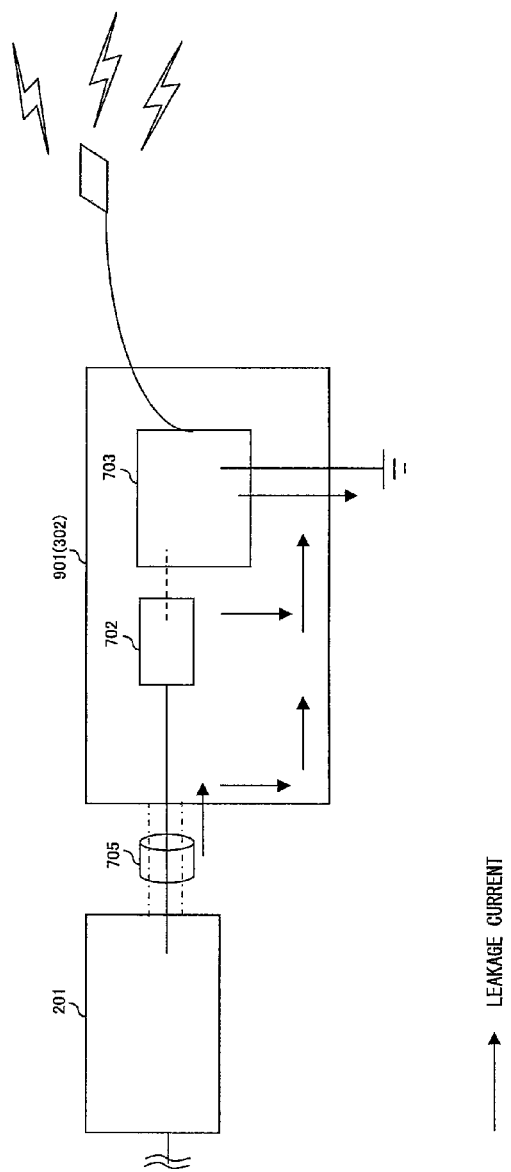
FIG. 9 is an explanatory view of a leakage current.

FIG. 9 is an explanatory view of a leakage current. For example, an electric knife device 901 of a specific manufacturer is connected as the medical equipment 302.

Under the environment of the shielding effect shown in FIG. 8, the electric knife device 901 is driven. Then, as shown in FIG. 9, there can be the case in which a leakage current passing from the communication converter 201 to the electric knife device 901 flows into the grounding portion. There also can be the case in which a leakage current generated from an electronic element on the substrate in the electric knife device 901 flows into the grounding portion.

Since medical equipment is normally protectively grounded as shown in FIG. 9, a leakage current within a predetermined value does not cause a specific influence of the leakage current. However, some connected medical equipment units can receive an amount of leakage current exceeding a predetermined value when the shielding effect is intensified.

For example, the medical equipment A of a firm A receives a small influence of a leakage current although the shielding effect is high, but the medical equipment B of a firm B can receive a large influence of a leakage current when the shielding effect is high. Then, by adjusting the grounding state of the device side communication system substrate 611 of the communication converter 201, the shielding effect and the effect of a leakage current are adjusted.

Figure 10:
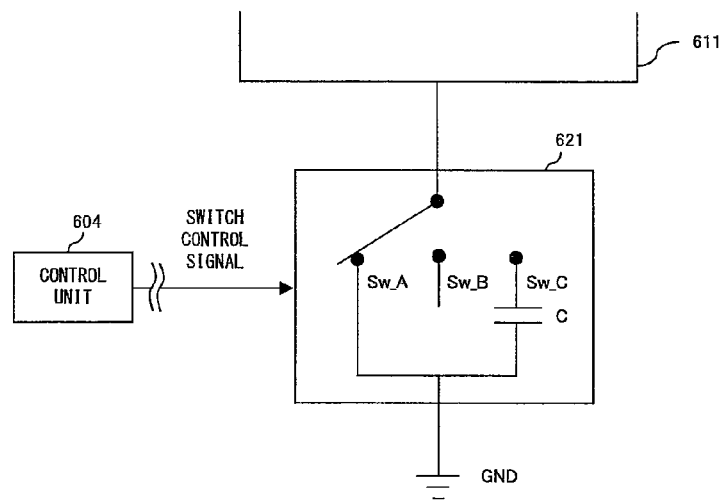
FIG. 10 shows an example of a grounding switch unit 621 according to the first embodiment of the present invention.

FIG. 10 shows an example of the grounding switch unit 621 according to the present invention. According to a switch control signal from the control unit 604, the grounding switch unit 621 is switched to any of terminal Sw_A, terminal Sw_B, and terminal Sw_C.

FIG. 11 shows the relationship between the noise and leakage current by switching of the grounding switch unit 621 according to the present embodiment. Each medical equipment unit is checked in advance for the shielding effect and the influence of the leakage current by the presence/absence of grounding, and classified into any of the switching types 'A' through 'C'. The relationship shown in FIG. 11 is described below with reference to FIG. 10.

When the switching type of the medical equipment 302 connected to the communication converter 201 is 'A', the grounding switch unit 621 is switched to the terminal Sw_A. As a result, the device side communication system substrate 611 is connected to the GND. In this case, the shielding effect is intensified. Therefore, the noise can be reduced (refer to FIG. 8). While the leakage current increases (FIG. 9), the amount of increase is allowable.

When the switching type of the medical equipment 302 connected to the communication converter 201 is 'B', the grounding switch unit 621 is switched to the terminal Sw_B. As a result, the connection between the device side communication system substrate 611 and the GND is released. In this case, the device side communication system substrate 611 is isolated from the metal housing 405 and the control system substrate 601. Then, the leakage current from the control system substrate 601 can be prevented from passing to the device side communication system substrate 611. Thus, the leakage current passing from the communication converter 201 to the medical equipment 302 can be suppressed. As a result, the influence of the leakage current in the medical equipment 302 can be suppressed. On the other hand, the suppressed shielding effect increases the noise.

When the switching type of the medical equipment 302 connected to the communication converter 201 is 'C', the grounding switch unit 621 is switched to the terminal Sw_C. As a result, the device side communication system substrate 611 is connected to the GND through the capacitor C. Using the capacitor C, the device side communication system substrate 611 can be connected to the GND at a high frequency. Therefore, when a high frequency is generated, the device side communication system substrate 611 is connected to the GND at a high frequency, thereby enhancing the shielding effect and decreasing the noise. Furthermore, since the device side communication system substrate 611 is not electrically short-circuited to the GND, the leakage current can also be decreased.

FIG. 12 shows an example of the grounding information by equipment according to the present embodiment. Whether or not the influence of a leakage current is high with respect to the shielding effect depends on the manufacturer of medical equipment or on each medical equipment unit. Therefore, the switching type information about each medical equipment unit is stored as the grounding information 1201 by equipment in the memory 606.

For example, when the control unit 604 detects a connection with medical equipment P1, the unit acquires the switching type 'A' of the medical equipment P1 from the grounding information 1201 by equipment. Then, the control unit 604 transmits to the grounding switch unit 621a switch control signal for switching to the terminal Sw_A. The grounding switch unit 621 switches to the terminal Sw_A according to the switch control signal.

Figure 13A:
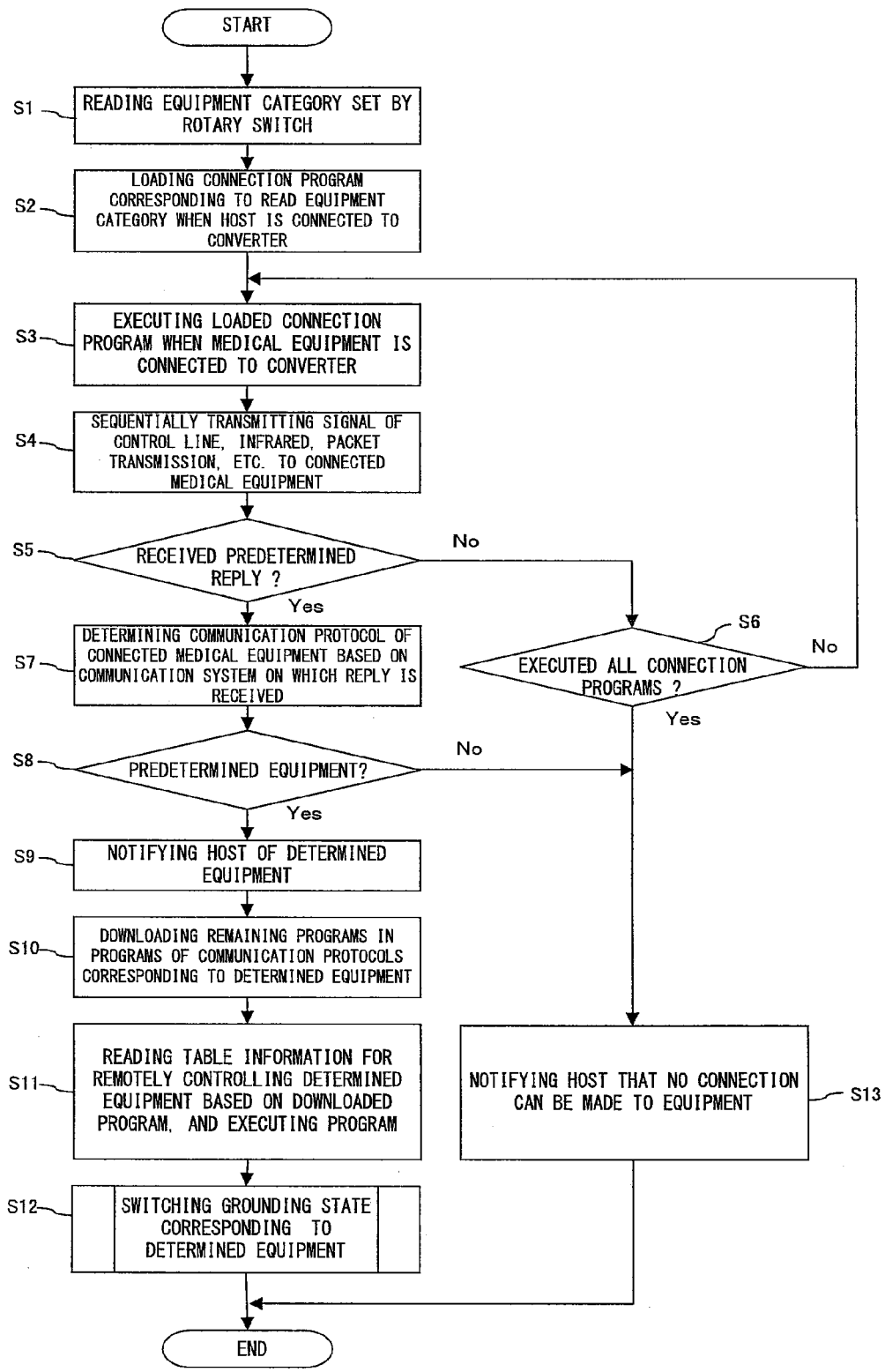
FIGS. 13A and 13B show the operation flow of the communication converter according to the first embodiment of the present invention.
Figure 13B:
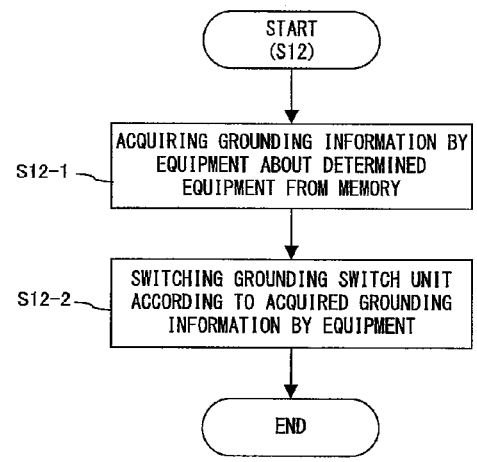

FIGS. 13A and 13B are operation flowcharts of the communication converter according to the present embodiment. First, a user switches a rotary switch (selection switch 501) to select the category of medical equipment to be connected to the communication converter 201. Then, the control unit 604 reads the equipment category set by a rotary switch (S1).

Next, when the communication converter 201 and the host 301 are connected, the communication converter 201 downloads the connection program of the medical equipment corresponding to the equipment category read in S1 from the host 301. The downloaded connection program is stored in the memory 606.

Next, when the communication converter 201 is connected to any medical equipment, the communication converter 201 reads any connection program stored in the memory 606 and executes the program (S3). Then, the communication converter 201 determines the communication system of target medical equipment by sequentially transmitting a signal of a control line, infrared, packet transmission, etc. to the connected medical equipment (hereinafter referred to as target medical equipment) (S4). That is, when a reply is received from target medical equipment in response to the transmission from the communication converter 201, it can be determined that the communication system of the target medical equipment is the communication system (for example, infrared communication, Ethernet communication, USB, etc.) in which the reply is received.

Until a reply is received from the target medical equipment, the communication converter 201 sequentially executes the downloaded connection program, and sequentially transmits to each target medical equipment unit a signal of a control line, infrared, a packet transmission, etc. (repeating S3 and S4). When there is no reply received from the target medical equipment even after all downloaded connection programs are executed (NO in S5, YES in S6), the host 301 is notified that there is no connection program corresponding to the target medical equipment (S13).

If there is a reply from the target medical equipment (YES in S5), the communication converter 201 determines the communication protocol of the target medical equipment on the basis of the communication system in which the reply was received (S7). In the method of determining the communication protocol of target medical equipment, for example, the communication converter 201 sequentially performs a sequence of detecting a bit rate, a sequence of detecting the ID related to the reply, a sequence of detecting the header in a packet, etc. If the target medical equipment can be determined, the communication protocol of the target medical equipment can be designated on the basis of the determination result. For example, in the case of the RS-232C, a communication protocol can be designated by determining the difference in transfer speed (bit rate) and the difference in message. In the case of the USB, a communication protocol can be designated by determining the difference in, for example, descriptor or procedure. In addition, in the case of a parallel communication, a communication protocol can be designated by determining the difference in signal pattern etc.

If the communication protocol of the target medical equipment cannot be determined as a result of checking the communication protocol in S7, or if the communication protocol of the target medical equipment can be determined but the target medical equipment is not the predetermined one (NO in S8), then the communication converter 201 notifies the host 301 that there is no connection program corresponding to the target medical equipment (S13).

On the other hand, if the target medical equipment is determined as predetermined medical equipment by designating a communication protocol as a result of determining the communication protocol in S7 (YES in S8), then the communication converter 201 notifies the host 301 of the determined medical equipment (S9).

Upon receipt of the notification of the determination result in S9, the host 301 transmits the remaining programs except the connection program in the communication programs corresponding to the target medical equipment. The communication converter 201 receives the remaining programs from the host 301 (S10). The communication converter 201 merges the remaining programs and an already stored connection program as one communication program.

The communication program downloaded by the communication converter 201 can be a program other than the remaining programs downloaded by the communication converter 201. For example, all communication programs corresponding to the medical equipment including the connection program can be completely downloaded.

The control unit 604 reads a table storing the status information for remote control of the target medical equipment from the communication program, and executes the communication program (S11). Thus, communications can be established between the host 301 and the target medical equipment through the communication converter 201, and the host 301 can remotely control the target medical equipment.

Then, the control unit 604 switches the grounding state of the device side communication system substrate 611 by the grounding switch unit 621 corresponding to the determined medical equipment (S12). Practically, the control unit 604 acquires the switching type of the determined medical equipment from the grounding information 1201 by equipment stored in the memory 606 (S12-1). Then, the control unit 604 transmits to the grounding switch unit 621a switch control signal indicating switching to the terminal corresponding to the switching type. The grounding switch unit 621 switches to any appropriate terminal according to the switch control signal (S12-2).

According to the present embodiment, when a medical equipment unit is connected, the communication converter automatically determines the medical equipment, and can easily change the grounding environment depending on the medical equipment. Thus, the shielding effect and the influence of the leakage current can be adjusted.

<Second Embodiment>

In the present embodiment, the communication converter includes an internal substrate separated at plural portions. The same components described with reference to the first embodiment are assigned the same reference numerals, and the detailed descriptions are omitted here.

Figure 14:
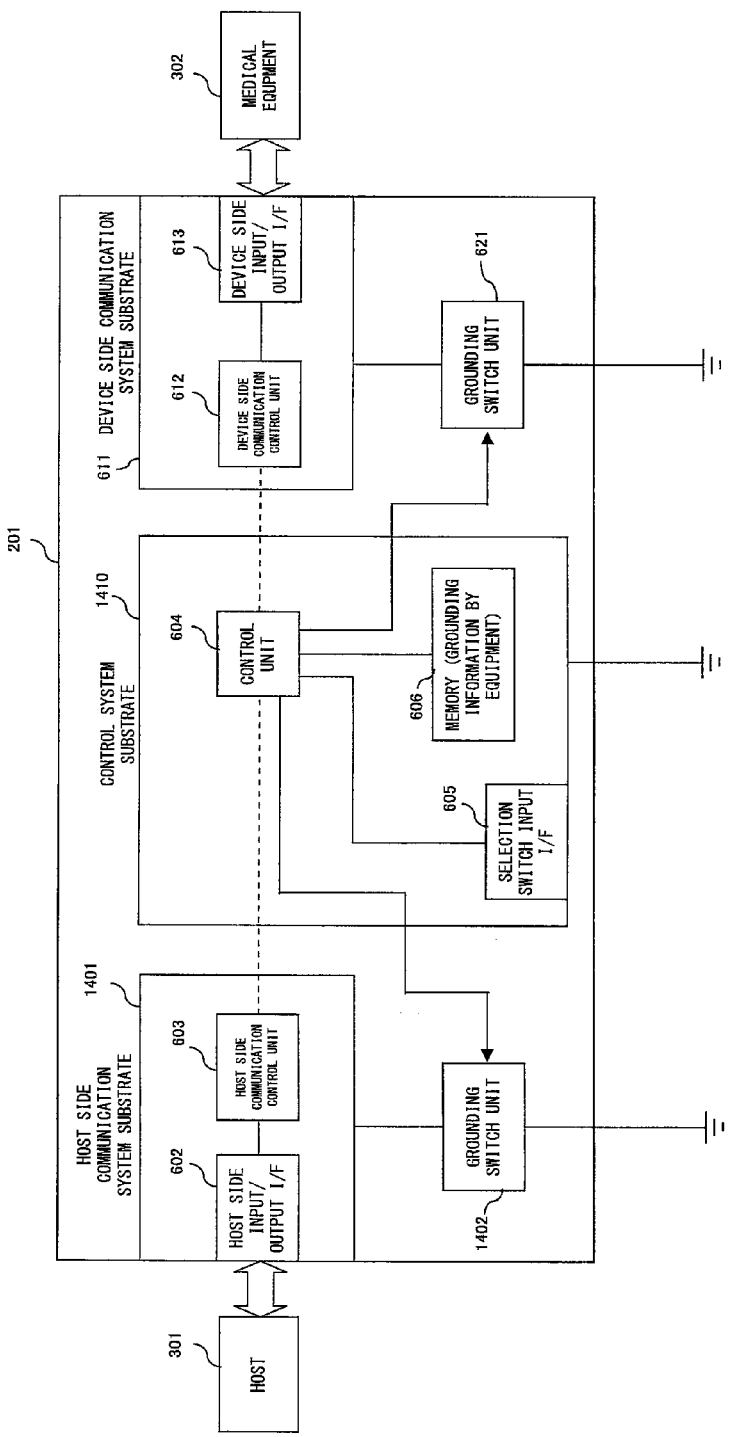
FIG. 14 shows the outline of the configuration inside the communication converter according to the second embodiment of the present invention.

FIG. 14 shows the outline of the internal configuration of the communication converter according to the present embodiment. FIG. 14 shows the control system substrate 601 separated into a host side communication system substrate 1401 and a control system substrate 1410, and also shows an additional grounding switch unit 1402. The host side communication system substrate 1401 is provided with the host side input/output I/F 602 and the host side communication control unit 603. The host side communication system substrate 1401 is electrically isolated from the metal housing 405, the control system substrate 601, and the device side communication system substrate 611 unless it is grounded by the grounding switch unit 1402. The host side communication control unit 603 receives an instruction from the control unit 604 and communicates data with the control unit 604 through insulating elements such as a photo-coupler etc.

The grounding switch unit 1402 switches the grounding state of the host side communication system substrate 1401 at an instruction of the control unit 604. Like the grounding switch unit 621, the host side communication system substrate 1401 is an analog switch, a relay switch, etc.

Figure 15:
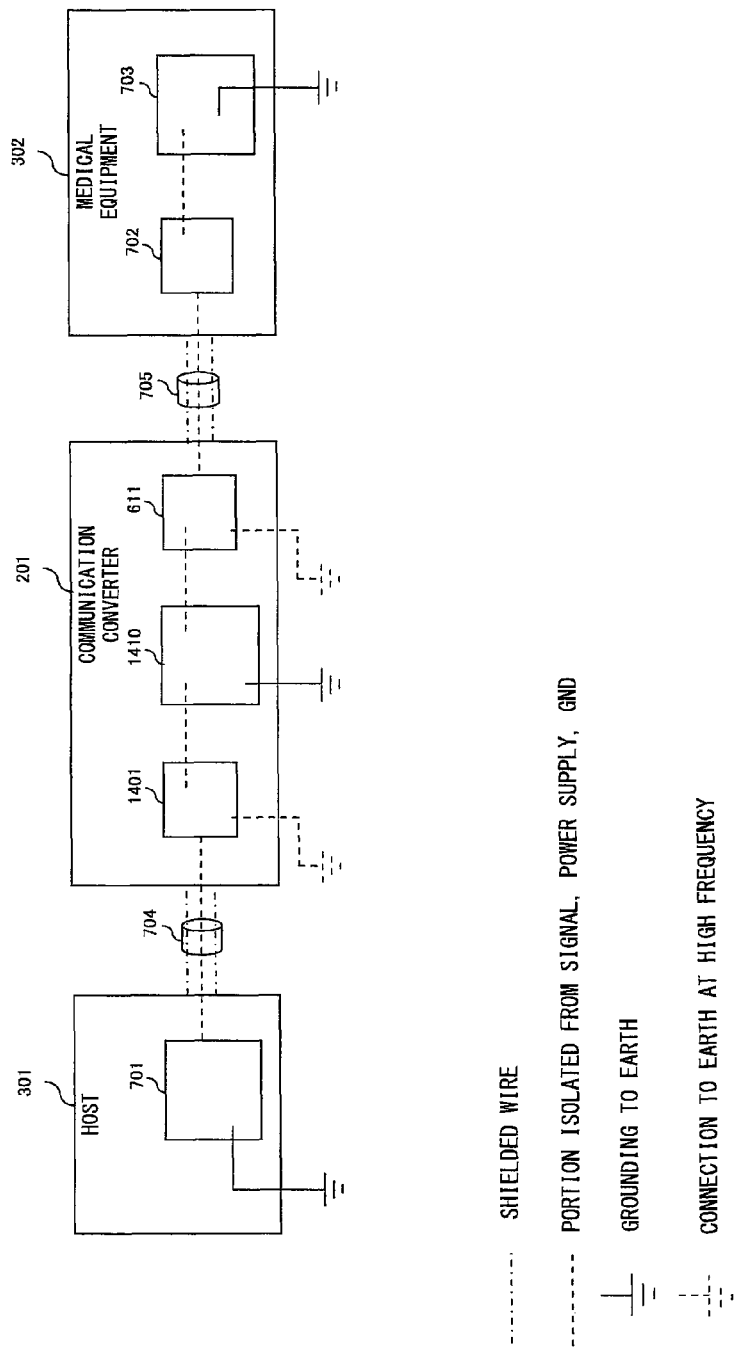
FIG. 15 shows the concept relating to the electric connection among the host computer 301, the communication converter 201, and the medical equipment 302 according to the second embodiment of the present invention.

FIG. 15 shows the concept of the electric connection among the host 301, the communication converter 201, and the medical equipment 302 according to the present embodiment. FIG. 15 shows an example of using capacitors as the grounding switch units 621 and 1402. Therefore, each of the device side communication system substrate 611 and the host side communication system substrate 1401 is grounded at a high frequency.

Thus, when a high frequency occurs, the device side communication system substrate 611 is connected to the GND, and the host side communication system substrate 1401 is connected to the GND at a high frequency, thereby enhancing the shielding effect, decreasing generated noise, and reducing the influence of external noise. Furthermore, since there is no electrical short circuit between the device side communication system substrate 611 and the GND or between the host side communication system substrate 1401 and the GND, a leakage current can be suppressed.

As in the first embodiment of the present invention, each of the grounding switch units 621 and 1401 can be switched to not only terminal Sw_C, but also terminal Sw_A or terminal Sw_B. The process shown in FIG. 13B can also be performed on each of the grounding switch units 621 and 1401.

According to the present embodiment, not only the medical equipment 302 but also the host 301 is isolated. Therefore, they can be free of the influence of each other. In addition, for example, even if one grounding switch unit is destroyed, the ground switching can be performed so far as the other grounding switch unit is effectively operated. Therefore, the ground switching can be performed more stably.

In the present embodiment, there are two pairs of an electrically isolated substrate and a grounding switch unit 621. However, the present invention is not limited to this application. For example, as shown in FIG. 16, there can be three or more pairs of an electrically isolated substrate and a grounding switch unit.

Figure 16:
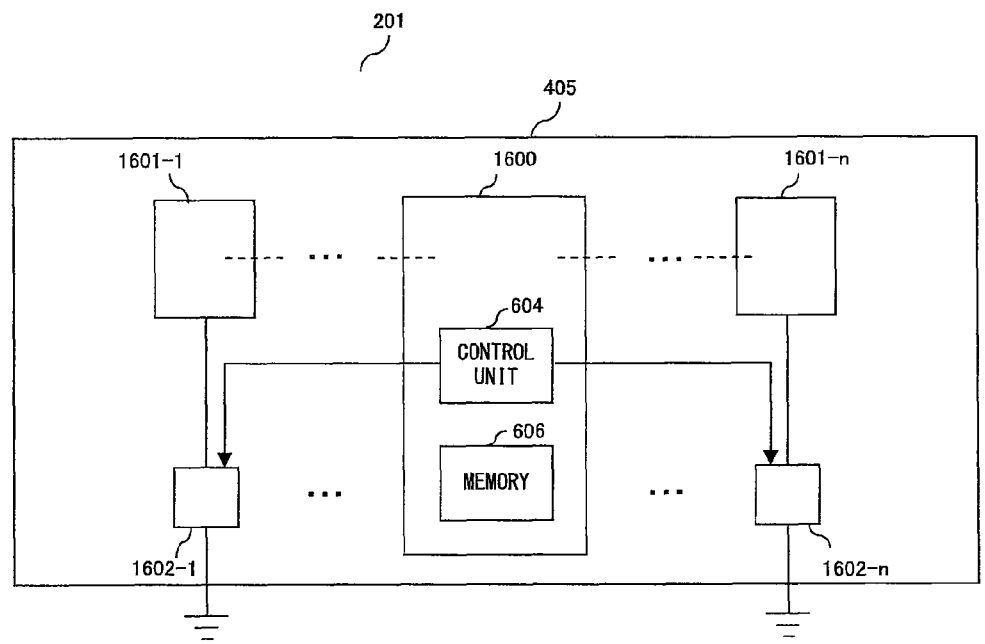
FIG. 16 shows the communication converter according to the second embodiment (variation example) of the present invention.

FIG. 16 shows the communication converter in the present embodiment (variation example). The metal housing of the communication converter 201 includes a primary substrate 1600 and n pieces of secondary substrate 1601. Each of the secondary substrate 1601 (1601-1 through 1601-*n*) is electrically isolated from each other, and also electrically isolated from the metal housing and the primary substrate 1600. Grounding switch units 1602 (1602-1 through 1602-*n*) are provided corresponding to each of the secondary substrate 1601. Like a control system substrate 1410, the primary substrate 1600 is provided with the control unit 604 and the memory 606. When n=1, it corresponds to the first embodiment. When n=2, it corresponds to the second embodiment.

FIG. 17 shows an example of grounding information by equipment according to the present embodiment (variation example). Grounding information 1701 by equipment includes setting information of each grounding switch unit for each medical equipment unit 302. When medical equipment is connected to the communication converter 201, the control unit 604 reads the grounding information 1701 by equipment corresponding to the medical equipment from the memory 606. Then, the control unit 604 controls each grounding switch unit (1602-1 through 1602-*n*) as described above with reference to FIG. 13B according to the grounding information 1701 by equipment.

Thus, the communication converter 202 includes a primary substrate 1600, n (n indicates any integer) pieces of secondary substrate 1601, and n pieces of grounding switch unit 1602. The primary substrate 1600 is provided with the control unit 604 for controlling the communication converter 201. The secondary substrate 1601 is electrically isolated from the primary substrate 1600 and the housing 405 of the communication converter 201. With n≧2, the secondary substrates 1601 are electrically isolated from one another. Any one of the secondary substrates 1601 is provided with the first communication control unit 612 for communication with the medical equipment 302 or the second communication control unit 603 for communication with the medical control device 301. The grounding switch unit 1602 corresponds to each of the n pieces of secondary substrate 1601, and switches the grounding state of the secondary substrate 1601. When the medical equipment 302 is connected, the control unit controls the grounding switch unit corresponding to the medical equipment 302.

The communication converter 201 further includes a memory 606 for storing grounding information about the grounding of the secondary substrate 1601. When the medical equipment 302 is connected, the control unit 604 reads grounding switch information corresponding to the medical equipment, and can control the grounding switch unit according to the read grounding information.

Each of the secondary substrates can be grounded through a capacitor by the grounding switch unit 1602 corresponding to the secondary substrate.

Thus, since each grounding switch unit can be adjusted, the range of the entire shield can be adjusted in detail. Therefore, the influence of the leakage current of the medical equipment based on the shielding effect can be strictly adjusted.

According to the present invention, when medical equipment is connected, the communication converter determines the medical equipment, and can easily change the grounding environment of the medical equipment. Thus, the shielding effect and the influence of the leakage current can be appropriately adjusted.

What is claimed is:

1. A communication converter configured to convert a communication system and/or a communication protocol to enable communications to be performed between medical equipment and a medical control device for controlling the medical equipment, comprising:

a primary substrate on which a control unit configured for controlling the communication converter is arranged;

n (n indicates any integer) pieces of secondary substrates electrically isolated from the primary substrate and a housing of the communication converter;

a storage unit configured for storing grounding information about grounding secondary substrate for each medical equipment;

n pieces of grounding switch units corresponding to each of the n pieces of secondary substrates configured for switching a grounding state of the secondary substrates; and a switching control unit configured for, when the medical equipment is connected, controlling to switch the grounding switch unit according to the grounding information corresponding to the medical equipment read from the storage unit.

2. The communication converter according to claim 1, wherein: when n≧2, the secondary substrates are electrically isolated from each other.

3. The communication converter according to claim 1, wherein:

any one of the secondary substrates is provided with one of a first communication control unit for communicating with the medical equipment and a second communication control unit for communicating with the medical control device.

4. An operation system comprising a medical equipment, a medical control device configured for controlling the medical equipment, and a communication converter configured for converting a communication system and/or a communication protocol to enable communications to be performed between the medical equipment and the medical control device for controlling the medical equipment, wherein:

the communication converter comprises:

a primary substrate on which a control unit configured for controlling the communication converter is arranged;

n (n indicates any integer) pieces of secondary substrates electrically isolated from the primary substrate and a housing of the communication converter;

a storage unit configured for storing grounding information about grounding the secondary substrate for each medical equipment;

n (n indicates any integers) pieces of switching unit corresponding to each of the n pieces of secondary substrate, configured for switching a grounding state of the secondary substrates; and a switching control unit configured for, when the medical equipment is connected, controlling to switch the grounding switch unit according to the grounding information corresponding to the medical equipment read from the storage unit.

5. A method for adjusting a grounding state of a communication converter which converts a communication system and/or a communication protocol to enable communications to be performed between medical equipment and a medical control device for controlling the medical equipment, wherein:

the communication converter comprises:

a primary substrate on which a control unit for controlling the communication converter is arranged;

n (n indicates any integer) pieces of secondary substrates electrically isolated from the primary substrate and a housing of the communication converter;

n (n indicates any integer) pieces of grounding switch unit corresponding to each of the n pieces of secondary substrates for switching a grounding state of the secondary substrates;

a storage unit for storing grounding information relating to grounding of an i-th (i =1~n) secondary substrate for each unit of the medical equipment; and a switching control unit, wherein the method comprises a step of:

when the medical equipment is connected, the switching control unit reads the grounding information corresponding to the medical equipment from the storage unit, and controls to switch the grounding switch unit according to the grounding information.

6. The communication converter according to claim 1, further comprising:

a determination unit configured for determining the connected medical equipment, wherein the switching control unit is configured to read the grounding information corresponding to the medical equipment determined by the determination unit from the storage unit, and to switch the grounding switch unit according to the read grounding information.

7. The communication converter according to claim 6, wherein:

the grounding switch unit is configured to switch a grounding state of the secondary substrates to any of a first state in which the secondary substrates and the ground are connected, a second state in which the secondary substrates and the ground are not connected, and a third state in which the secondary substrates and the ground are connected through a capacitor according to the control of the switching control unit.

8. The communication converter according to claim 7, wherein:

when the medical equipment determined by the determination unit is first medical equipment, the switching control unit reads first grounding information corresponding to the first medical equipment from the storage unit, controls the grounding switch unit according to the read first grounding information, and switches the grounding state of the secondary substrates to the first state.

9. The communication converter according to claim 7, wherein:

when the medical equipment determined by the determination unit is second medical equipment, the switching control unit reads second grounding information corresponding to the second medical equipment from the storage unit, controls the grounding switch unit according to the read second grounding information, and switches the grounding state of the secondary substrates to the second state.

10. The communication converter according to claim 7, wherein:

when the medical equipment determined by the determination unit is third medical equipment, the switching control unit reads third grounding information corresponding to the third medical equipment form the storage unit, controls the grounding switch unit according to the read third grounding information, and switches the grounding state of the secondary substrates to the third state.

* * * * *